United States Patent

Chang

Patent Number: 5,287,609
Date of Patent: Feb. 22, 1994

[54] SYRINGE DISPOSAL SYSTEM

[76] Inventor: Chin-Ming Chang, No. 7, Lane 218, Chung-Shan Rd., Sha-Lu Chen, Taichung Hsien, Taiwan

[21] Appl. No.: 74,787

[22] Filed: Jun. 10, 1993

[51] Int. Cl.$^5$ .............................................. B23Q 41/00
[52] U.S. Cl. .................................. 29/33 R; 128/919; 604/263
[58] Field of Search ............... 29/33 R, 426.5, 240, 29/564.3, 564.1, 564.7; 128/919; 604/263, 199, 111; 206/370, 366, 210, 364, 365

[56] References Cited

U.S. PATENT DOCUMENTS

| | | | |
|---|---|---|---|
| 4,989,307 | 2/1991 | Sharpe et al. | 29/240 |
| 5,067,949 | 11/1991 | Freundlich et al. | 604/263 |
| 5,075,529 | 12/1991 | Kudo | 128/919 X |
| 5,168,612 | 12/1992 | Schultz et al. | 29/33 R |

FOREIGN PATENT DOCUMENTS

| | | | |
|---|---|---|---|
| 4103562 | 8/1991 | Fed. Rep. of Germany | 128/919 |
| 2621825 | 4/1989 | France | 604/110 |
| 8701634 | 2/1989 | Netherlands | 128/919 |

*Primary Examiner*—William Briggs
*Attorney, Agent, or Firm*—Ladas & Parry

[57] ABSTRACT

A syringe disposal system includes a frame body and a separation device which includes an upper cover that is mounted on the frame body and that is formed with a needle guiding port. A driving gear is rotatably mounted on the frame body below the cover. A driven gear is rotatably mounted on the frame body below the cover and is positioned parallel to the driving gear. The teeth on the driven gear mesh with the teeth on the driving gear. A container is disposed below the driving and driven gears. The syringe disposal system also includes a fragmentation device which includes an inclined cutting plate, which has an outer side that is fixed on the frame body and an inner side that extends downwardly and inwardly and that is formed with spaced cutting teeth. A cutting wheel is rotatably mounted on the frame body below the inclined cutting plate and has spaced rows of axially-aligned cutting teeth extending radially. The cutting teeth on each row are able to mesh with the cutting teeth on the inclined cutting plate. A receptacle is disposed in the frame body below the cutting wheel.

7 Claims, 9 Drawing Sheets

SYRINGE DISPOSAL SYSTEM

BACKGROUND OF THE INVENTION

1. Field of the Invention

This invention relates to a medical waste disposal system, more particularly to a syringe disposal system.

2. Description of Related Art

Generally speaking, a conventional medical waste disposal system disposes a syringe without the separation of a needle from a barrel portion of the syringe. Thus, the needle and the barrel portion cannot be collected respectively for reuse. Such a method is not economical.

SUMMARY OF THE INVENTION

Therefore, the objective of this invention is to provide a syringe disposal system in which a needle can be separated from a barrel portion so that the needle and the barrel portion can be collected respectively and in which the barrel portion can be fragmentated.

Accordingly, a syringe disposal system of this invention is used to dispose a syringe, which has a needle and a barrel portion, and includes a frame body and a separation device which is mounted in the frame body in order to separate the needle from the barrel portion. The separation device has an upper cover which is mounted on the frame body and which is formed with a needle guiding port. The needle guiding port has a diameter which is larger than the diameter of the needle but smaller than the diameter of the barrel portion. A driving gear is rotatably mounted in the frame body below the cover and is formed with a plurality of spaced teeth. A driven gear is mounted rotatably in the frame body below the cover and which is positioned parallel to the driving gear. The driven gear is formed with a plurality of spaced teeth which mesh with the teeth on the driving gear. The teeth on the driving gear and the driven gear pull the needle downward from the barrel portion so as to separate them during the insertion of the needle between the driving gear and the driven gear via the needle guiding port on the cover. A container is placed below the driving gear and the driven gear for receiving the separated needle.

In one preferred embodiment, the container is provided with a heating unit in order to heat and decontaminate the separated needle. In addition, the frame body is formed so as to include a pair of opposite guiding slots. The driven gear has a shaft with two ends. The separation device includes a pair of mounting seats which are mounted movably and respectively on the guiding slots and in which the two ends of the shaft of the driven gear are rotatably mounted. Each of the mounting seats has an elongated protrusion extending therefrom into a respective one of the guiding slots. A pair of screws are mounted respectively in the guiding slots. Each of the screws is axially aligned and spaced from the elongated protrusion of its respective mounting seat. A pair of nuts engage movably with the screws. The separation device further includes a pair of compression springs, each of which is sleeved around one of the screws and the elongated protrusion of its respective mounting seat and rests between the screw's nut and the mounting seat.

The syringe disposal system of this invention also has a fragmentation device for fragmentating the barrel portion of the syringe. The fragmentation device includes an inclined cutting plate which has an outer side that is fixed on the frame body and an inner side that extends downwardly and inwardly and that is formed with spaced cutting teeth. A cutting wheel is rotatably mounted on the frame body below the inclined cutting plate and has spaced rows of axially-aligned cutting teeth extending radially therefrom. The axially-aligned cutting teeth on each row are able to mesh with the cutting teeth on the inclined cutting plate. A receptacle is disposed in the frame body below the cutting wheel for receiving the fragmentated barrel portion.

In the preferred embodiment, the rows of axially-aligned cutting teeth on the cutting wheel includes three angularly spaced rows of cutting teeth. In addition, the fragmentating device may have a pair of guiding plates mounted opposite to one another on the frame body above the cutting plate for guiding the barrel portion onto the cutting plate. In addition, the fragmentating device has a tubular guiding member which is disposed between the cutting wheel and the receptacle for guiding the fragmentated barrel into the receptacle.

BRIEF DESCRIPTION OF THE DRAWINGS

Other features and advantages of the present invention will become apparent in the following detailed description of the preferred embodiment, with reference to the accompanying drawings, in which.

DETAILED DESCRIPTION OF THE PREFERRED EMBODIMENT

Referring to FIGS. 1 to 5, a syringe disposal system (1) of this invention has a frame body (10) and a separation device (20a) for separating a needle (e) of a syringe (W') from a barrel portion (W) of the syringe (W'). The separation device (20a) includes an upper cover (201a) which is mounted on the frame body (10) and which is formed with a needle guiding port (201) The needle guiding port (201) has a diameter which is larger than the diameter of the needle (e) but smaller than the diameter of the barrel portion (W), thereby only permitting the entrance of the needle (e).

A driving gear (22) is rotatably mounted on the frame body (10) below the upper cover (201a) and is formed with a plurality of teeth (b). The driving gear (22) has a shaft with two ends (221, 222). One end (221) is connected to a gear (A). The other end (222) is rotatably mounted on a bearing (24). A driven gear (23) is rotatably mounted on the frame body (10) below the cover (201a) and is positioned parallel to the driving gear (22). The driven gear (23) is formed with a plurality of teeth (c) which mesh with the teeth (b) on the driving gear (22) in order pull the needle (e) downwards from the barrel portion (W) so as to separate them when inserting the needle (e) between the driving gear (22) and the driven gear (23) via the needle guiding port (201) Referring again to FIGS. 1 to 3, a pair of mounting seats (26) are mounted movably and respectively inside a pair of elongated guiding slots (27a) which are formed on two opposite sides of the frame body (10). The driven gear (23) has a shaft with two ends (231) which are rotatably mounted on the mounting seats (26) by means of two bearings (25). Each of the mounting seats (26) has an elongated protrusion (261) extending therefrom into its respective guiding slot (27a). A pair of screws (29) are mounted in the guiding slots (27a). Each of the screws (29) is axially aligned and is spaced from the elongated protrusion (261) of the mounting seat (26). A pair of nuts (28) engage movably with their respective screws (29). A pair of compression springs (27) are provided. Each compression spring (27) is sleeved around the screw (29) and the elongated protrusion (261) and rests between the nut (28) and the mounting seat (26). The mounting seats (26) can be biased retractively by the compression springs (27). Thus, the driven gear (23) can be biased toward the driving gear (22) so that the teeth (b, c) can tightly pull the needle (e) downward from the barrel portion (W) and break the needle (e) into pieces. In addition, due to the provision of the nuts (28), the biasing force of each compression spring (27) can be adjusted.

A container (30) is disposed below the driving and driven gears (22, 23) for receiving the separated needle (e). The container (30) is provided with a heating unit (31) in order to heat and decontaminate the separated needle (e) therein.

Referring to FIGS. 1, 5 to 8B', the syringe disposal system of this invention further has a fragmentation device (40) for fragmentating the barrel portion (W) after separation. The fragmentation device (40) includes an elongated inclined cutting plate (41) which has an outer side (41a) that is fixed on the frame body (10) and an inner side (41a') that extends downwardly and inwardly. The inner side (41a') is formed with spaced cutting teeth (41b).

Figure 6:
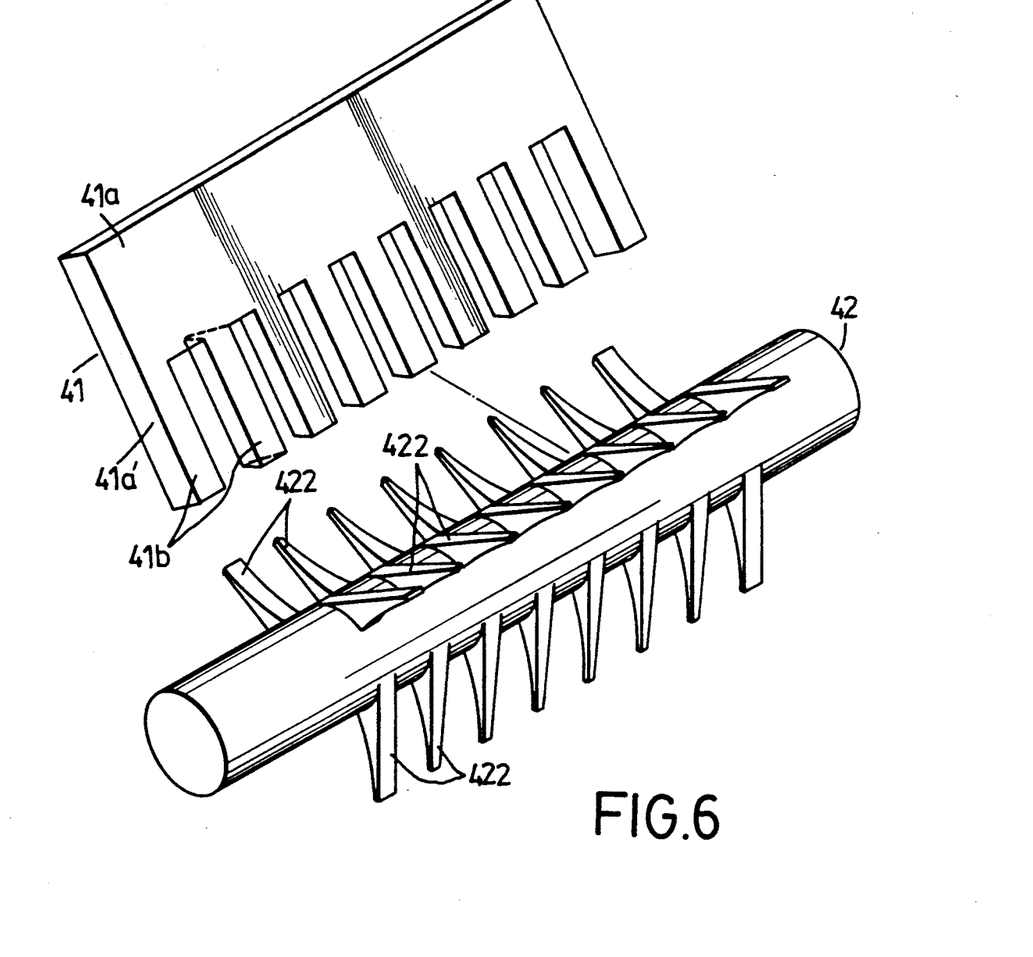
FIG. 6 is a perspective view of a cutting plate and a cutting wheel of the fragmentation device.
Figure 7:
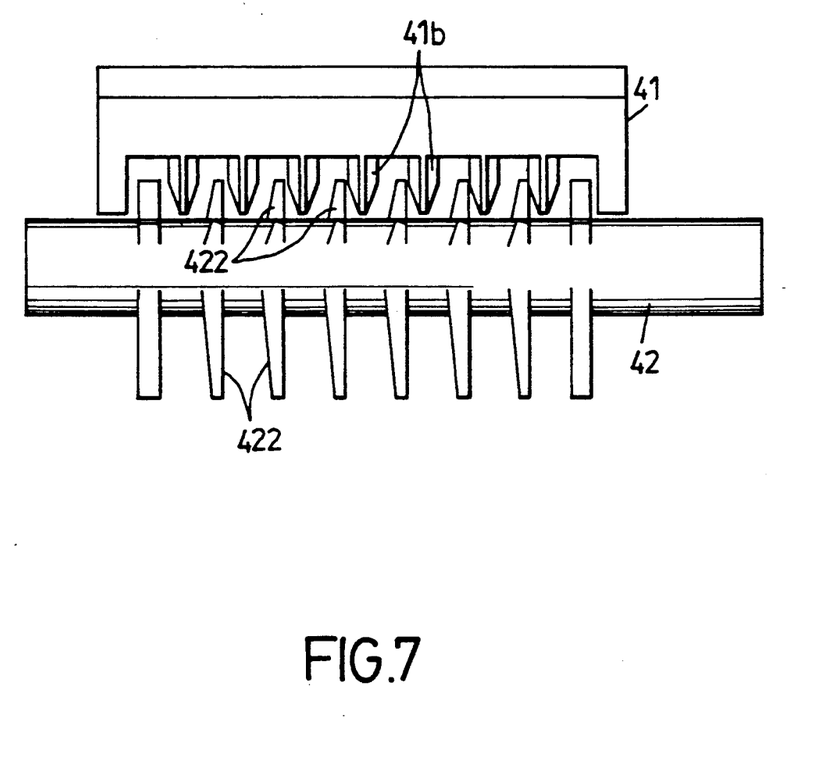
FIG. 7 is a schematic view showing the engagement between the cutting plate and the cutting wheel's teeth.

The fragmentation device (40) further includes an elongated cutting wheel (42) which is rotatably mounted on the frame body (10) below the inclined cutting plate (41). The cutting wheel (42) has two ends, one of which is connected to a gear (B) and the other is mounted in a bearing (43) that is positioned opposite to the gear (B). The cutting wheel (42) is formed with three angularly spaced rows of axially-aligned cutting teeth (422). The cutting teeth (422) on each row are able to mesh with the cutting teeth (41b) on the inclined cutting plate (41) so as to fragmentated the separated barrel portion (W).

Figure 5:
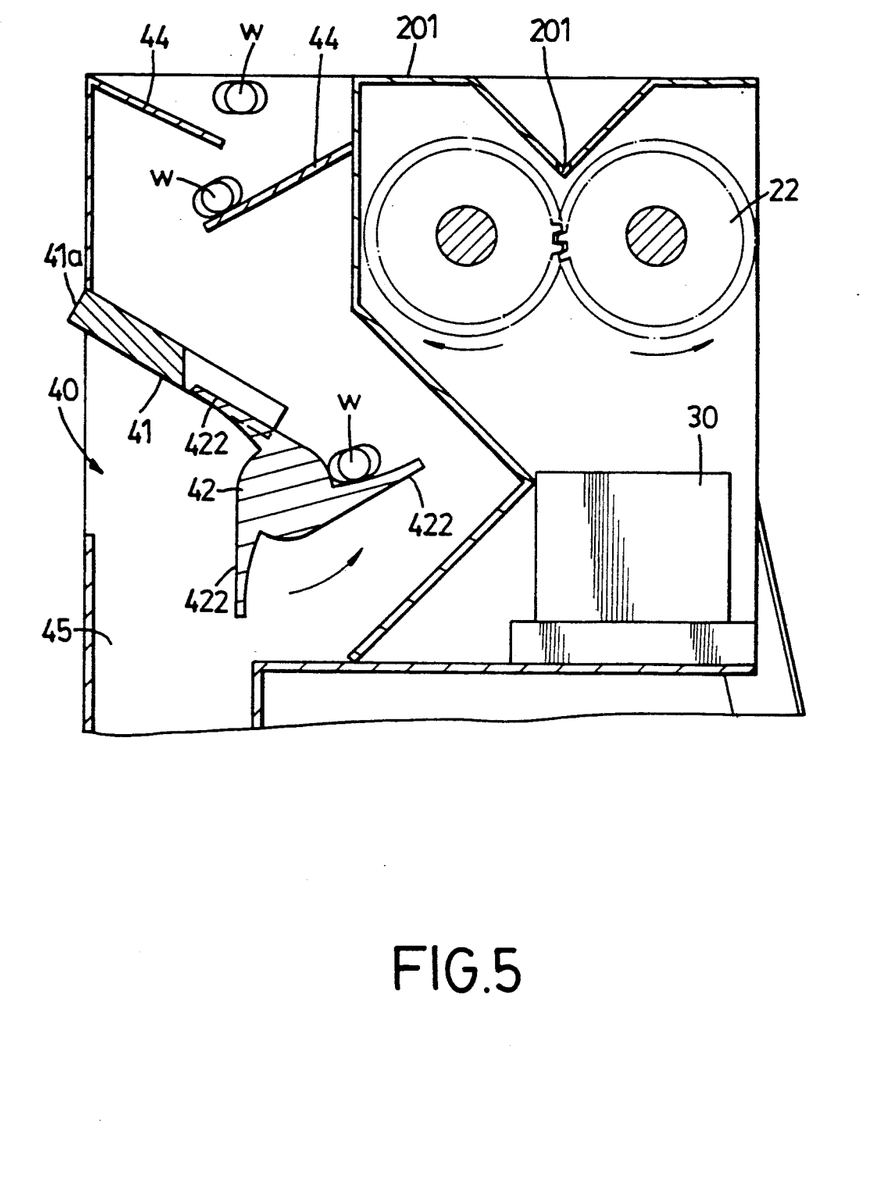
FIG. 5 is a partial sectional view of the separation device and the syringe disposal system's fragmentation device to show the operation thereof.

A pair of inclined guiding plates (44) are mounted opposite to one another on the frame body (10) above the cutting plate (41) in order to guide the barrel portion (W) onto the cutting plate (41) A receptacle (60) is disposed in the frame body (10) below the cutting wheel (42) for receiving the fragmentated barrel portion (W). In addition, a tubular guiding member (45) is placed between the cutting wheel (42) and the receptacle (60) for guiding the fragmentated barrel portion (W) into the latter.

Figure 1:
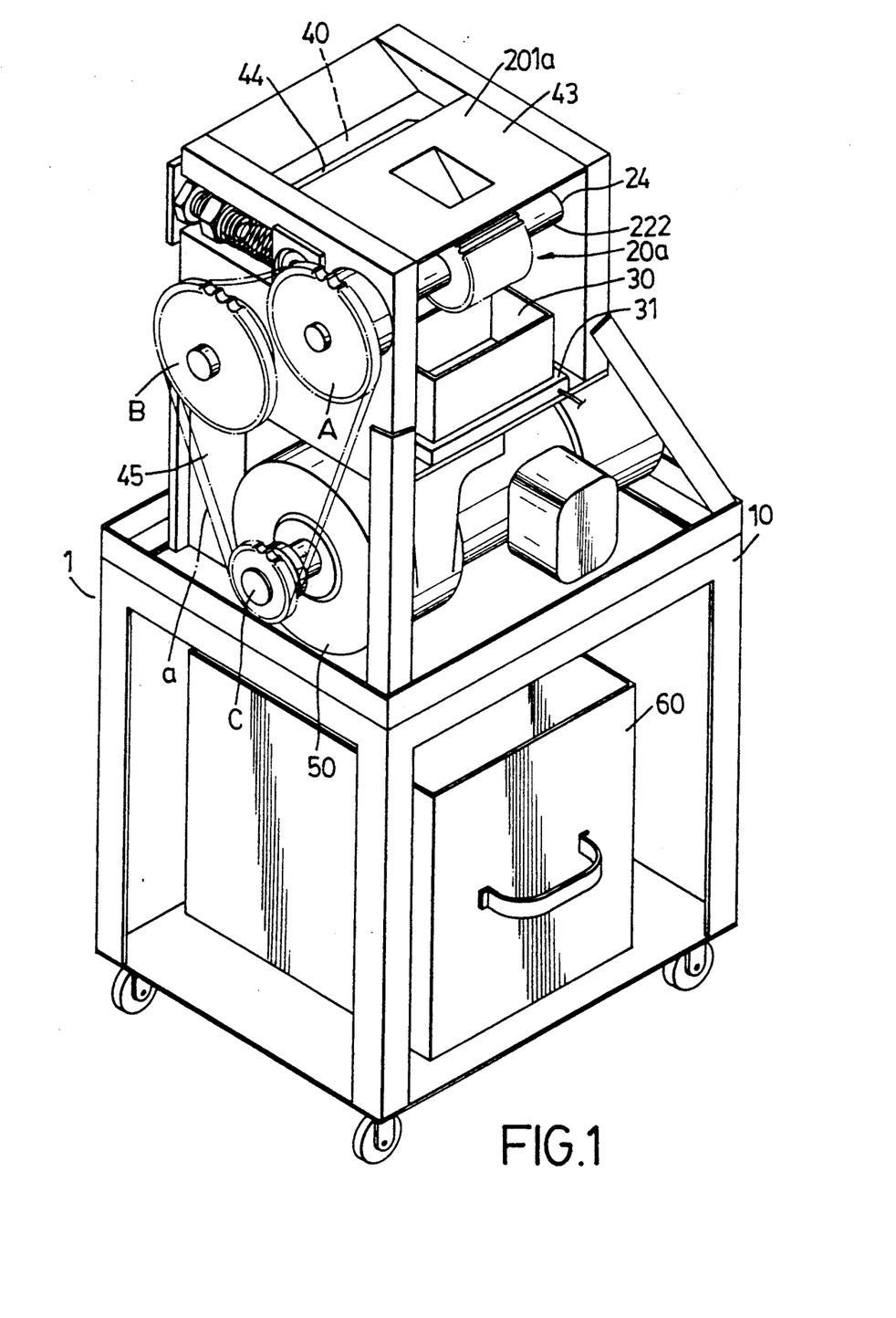
FIG. 1 is a perspective view of a syringe disposal system of this invention.
Figures 2A, 2B:
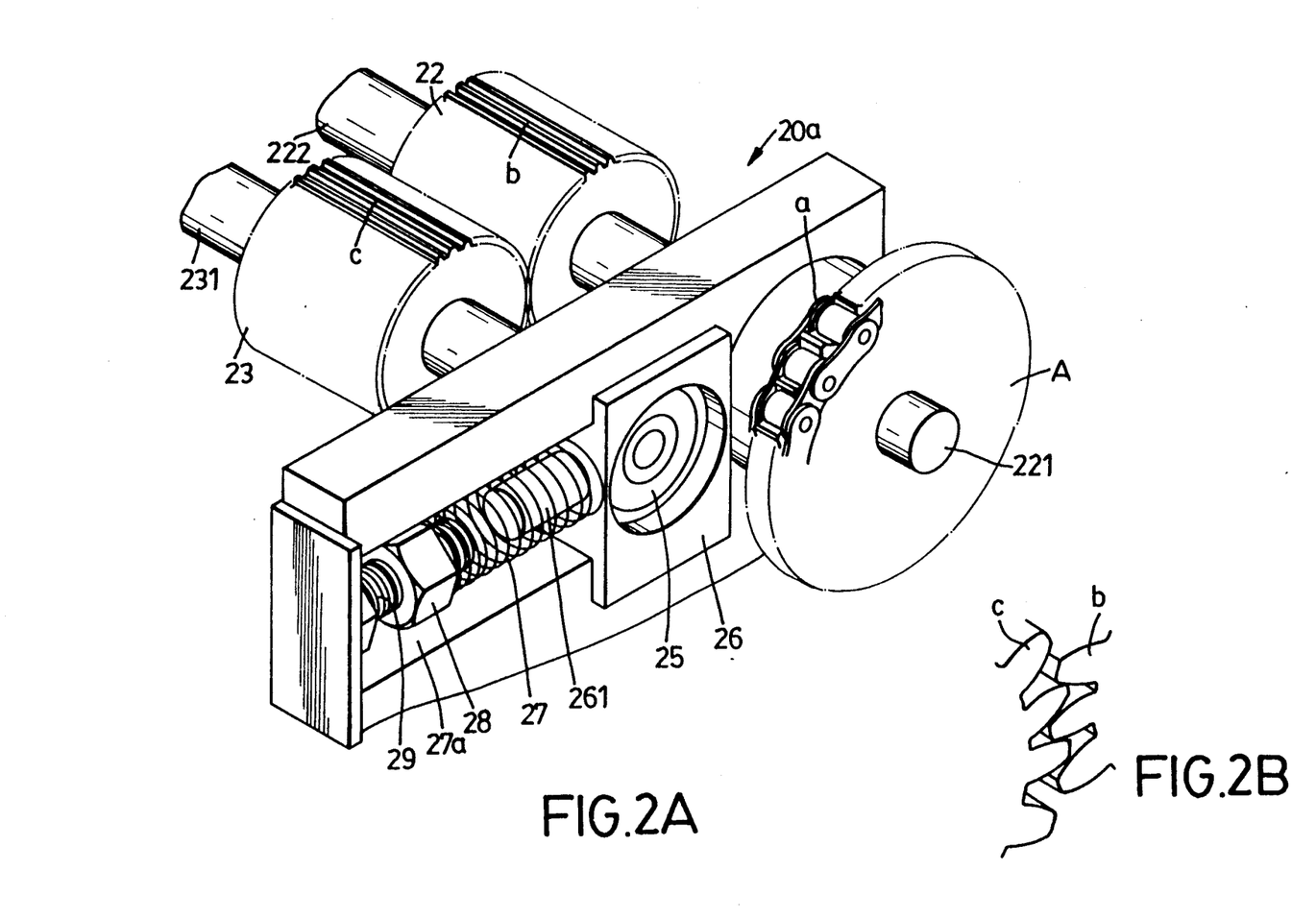
FIG. 2A is a partial schematic view of a separation device of the syringe disposal system of this invention.
FIG. 2B is an enlarged view showing the engagement between the teeth of the separation device's driving gear and driven gear.
Figure 3:
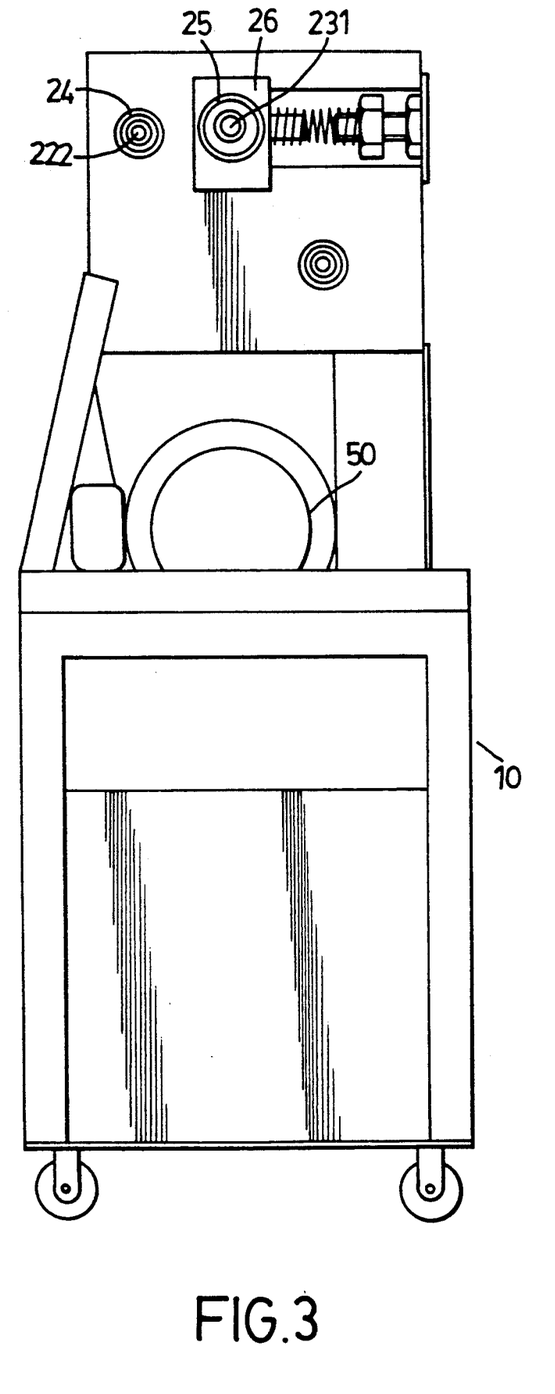
FIG. 3 is a side view of the syringe disposal system shown in FIG. 1.
Figure 4:
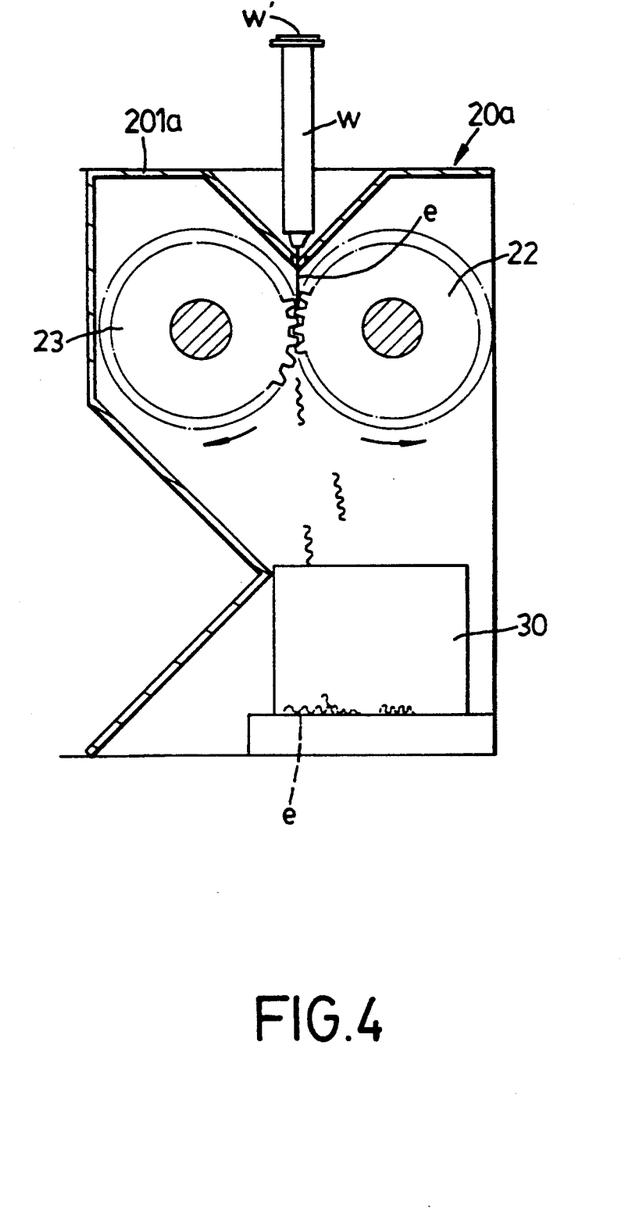
FIG. 4 is a partial sectional view of the separation device showing how a needle is separated from a barrel portion.

Referring again to FIGS. 1 and 2, the syringe disposal system of this invention further has a motor unit (50), a gear (C) which is connected to the motor unit (50), and a chain belt (a) which passes over the gears (A, B, C) in order to drive the driving gear (22), causing the cutting wheel (42) to rotate.

Figure 8A:
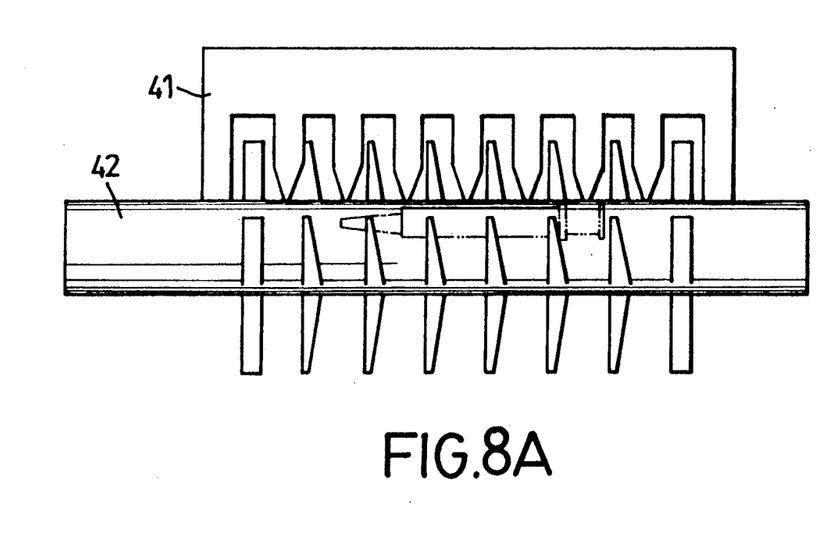
FIGS. 8A to 8B' are schematic views showing how the cutting plate and the cutting wheel work together to cut the barrel portion.
Figure 8B:
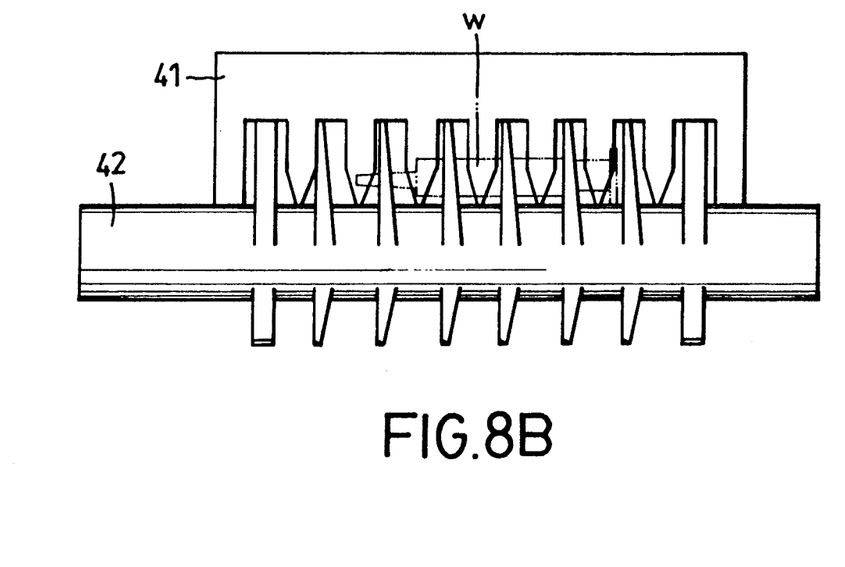

FIGS. 8A to 8B' show how the cutting plate (41) and the cutting wheel (42) work cooperatively to cut the barrel portion (W).

A needle (e) of a disposed syringe (W') can be inserted between the driving gear (22) and the driven gear (23) via the needle guiding port (201) and is separated from a barrel portion (W) of the syringe (W') when the driving gear (22) is actuated to rotate by the motor unit (50) and the chain belt (a). Afterwards, the separated barrel portion (W) can be put onto the cutting plate (41) via the guiding plates (44) and are fragmentated by means of the cutting plate (41) and the cutting wheel (42), which is actuated to rotate by the motor unit (50) and the chain belt (a).

Thus, according to the syringe disposal system of this invention, the needle (e) and the barrel portion (W) of the syringe (W') can be separated and the separated barrel portion (W) can be cut into pieces. The separated needle (e) and the fragmentated barrel portion (W) can be collected respectively for reuse.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

I claim:

1. A syringe disposal system for disposing a syringe which has a needle and a barrel portion, said syringe disposal system comprising frame body and a separation device which is mounted in said frame body for separating said needle from said barrel portion, said separation device including:
   an upper cover which is mounted on said frame body and which is formed with a needle guiding port, said needle guiding port having a diameter which is larger than the diameter of said needle but smaller than the diameter of said barrel portion;
   a driving gear which is rotatably mounted on said frame body below said cover and which is formed with a plurality of spaced teeth;
   a driven gear which is rotatably mounted on said frame body below said cover and which is positioned parallel to said driving gear, said driven gear being formed with a plurality of spaced teeth which mesh with said teeth on said driving gear, said teeth on said driving gear and said driven gear being able to pull said needle downward from said barrel portion when said needle is inserted between said driving gear and said driven gear via said needle guiding port on said cover, and
   a container which is placed below said driving gear and said driven gear for receiving the separated needle.

2. A syringe disposal system as claimed in claim 1, wherein said container is provided with a heating unit in order to decontaminate said separated needle.

3. A syringe disposal system as claimed in claim 1, wherein said frame body is formed with a pair of guiding slots placed opposite to one another, said driven gear having a shaft with two ends, said separation device further including a pair of mounting seats which are movably mounted to their respective guiding slots and in which said two ends of said shaft of said driven gear are rotatably mounted, each of said mounting seats having an elongated protrusion extending therefrom into a respective one of said guiding slots, a pair of screws which are mounted respectively inside said guiding slots, each of said screws being axially aligned and spaced from said elongated protrusion of one of said mounting seats, a pair of nuts each of which engages movably with one of said screws, and a pair of compression springs, each of which is sleeved around one of said screws and said elongated protrusion of one of said mounting seats and rests between one of said nuts and one of said mounting seats.

4. A syringe disposal system as claimed in claim 1, further comprising a fragmentation device for fragmentating said barrel portion of said syringe, said fragmentation device including:

an inclined cutting plate which has an outer side that is fixed on said frame body and an inner side that extends downwardly and inwardly and that is formed with spaced cutting teeth;

a cutting wheel which is rotatably mounted on said frame body below said inclined cutting plate, said cutting wheel having spaced rows of axially-aligned cutting teeth extending radially therefrom, said axially-aligned cutting teeth on each of said rows being able to mesh with said cutting teeth on said inclined cutting plate; and a receptacle being placed in said frame body below said cutting wheel for receiving the fragmentated barrel portion.

5. A syringe disposal system as claimed in claim 4, wherein said rows of axially-aligned cutting teeth on said cutting wheel includes three angularly spaced rows of cutting teeth.

6. A syringe disposal system as claimed in claim 4, wherein said fragmentating device further has a pair of guiding plates mounted opposite to one another on said frame body above said cutting plate for guiding said barrel portion onto said cutting plate.

7. A syringe disposal system as claimed in claim 4, wherein said fragmentating device further has a tubular guiding member which is placed between said cutting wheel and said receptacle for guiding said fragmentated barrel into said receptacle.

* * * * *